(12) United States Patent
Yang et al.

(10) Patent No.: US 6,987,396 B2
(45) Date of Patent: Jan. 17, 2006

(54) SENSOR ARRAY FOR ELECTROCHEMICAL CORROSION MONITORING

(75) Inventors: Lietai Yang, San Antonio, TX (US); Narasi Sridhar, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 10/764,906

(22) Filed: Jan. 26, 2004

(65) Prior Publication Data

US 2004/0155670 A1    Aug. 12, 2004

Related U.S. Application Data

(63) Continuation of application No. 10/106,427, filed on Mar. 26, 2002, now Pat. No. 6,683,463.

(60) Provisional application No. 60/279,061, filed on Mar. 27, 2001.

(51) Int. Cl.
*G01N 27/108* (2006.01)
*G01N 1/20* (2006.01)
(52) U.S. Cl. .................................. 324/700; 73/863.02
(58) Field of Classification Search ................ 324/700, 324/444, 437–451; 204/400, 404, 410–412
See application file for complete search history.

(56) References Cited

U.S. PATENT DOCUMENTS

| | | | | |
|---|---|---|---|---|
| 3,331,021 A | | 7/1967 | Marsh et al. ................ 205/775 |
| 3,924,175 A | * | 12/1975 | Wilson ........................ 324/444 |
| 4,158,806 A | * | 6/1979 | Kotylev et al. .............. 324/700 |
| 4,717,673 A | | 1/1988 | Wrighton et al. ............. 436/68 |
| 4,840,719 A | | 6/1989 | Jasinski ....................... 204/404 |
| 4,874,500 A | | 10/1989 | Madou et al. ............... 204/412 |
| 5,015,355 A | | 5/1991 | Schiessl ....................... 204/404 |
| 5,139,627 A | | 8/1992 | Eden et al. ............. 204/153.11 |
| 5,306,414 A | | 4/1994 | Glass et al. ................. 204/404 |
| 6,132,593 A | | 10/2000 | Tan ........................... 205/776.5 |
| 6,683,463 B2 | | 1/2004 | Yang et al. .................. 324/700 |

OTHER PUBLICATIONS

International Preliminary Examining Authority PCT/US02/09608, Nov. 15, 2002.
Steismo et al., "Aspects of testing and selecting stainless steels for sea water applications" 1994, Paper #492, Corrosion 94, Annual Conference of Corrosion show Sponsored by NACE International, no month available, 1994.
Sikora, J., et al.; "Analysis Current and Potential Oscillations on 304 SS During Metalstable Pitting", Proceedings of the Symposium on Critical Factors in Localized Corrosion III; The Electrochemical Society, Inc., Pennington, NJ; pp. 508518, no month available,1999.
Lumsden, J.B., et al.; "Electrochemical Noise for Carbon Steel in Sodium Chloride Solutions-Effect of Chloride and Oxygen Activity", Corrosion 92, Paper N0 224, The NACE Annual Conference, Houston, TX., no month available, 1992.

(Continued)

*Primary Examiner*—Vincent Q. Nguyen
(74) *Attorney, Agent, or Firm*—Baker Botts L.L.P.

(57) ABSTRACT

A sensor array for measuring localized corrosion based on electrochemical reactions is disclosed. The sensor has an array of electrodes that are made from the material of interest. The electrodes are electrically insulated from each other and arranged so that a small area of the electrode contacts a corrosive environment. The voltage outputs across the electrodes connected to the electrodes are measured and used as the signals to indicate localized corrosion.

13 Claims, 5 Drawing Sheets

OTHER PUBLICATIONS

Rothwell, A.N., et al.; "Electrochemical Noise Techniques for Determining Corrosion Rates and Mechanisms", Corrosion 92, Paper N0 223, The NACE Annual Conference, Houston, TX., no month avail., 1992.

Qingdong, Z.; "A Novel Electrochemical Testing Method and Its Use in the Investigation of Underfilm Corrosion of Temporary Protective Oil Coating", Corrosion, vol. 56, No. 7; pp. 722-726., no month avail., 2000.

Rogne, T., et al.; "Aspects of Teting and Selecting Stainless Steels for Sea Water Applications", The Annual Conference and Corrosion Show Sponsored by NACE International; Paper No. 492, no month avail., 1994.

Z. Fei, et al.,; Spatiotemporal Patterns on Electrode Arrays; J. Phys. Chem., vol. 100, No. 49, pp. 18986-18991.

* cited by examiner

SENSOR ARRAY FOR ELECTROCHEMICAL CORROSION MONITORING

RELATED PATENT APPLICATION

This application is a continuation of U.S. patent application Ser. No. 10/106,427 entitled "Sensor Array for Electrochemical Corrosion Monitoring," filed on Mar. 26, 2002 now U.S. Pat. No. 6,683,463 and claims the benefit of U.S. Provisional Application Ser. No. 60/279,061, filed Mar. 27, 2001 and entitled "Sensor Array For Electrochemical Corrosion Monitoring".

TECHNICAL FIELD OF THE INVENTION

This invention relates to sensors for detecting corrosion in metals, and more particularly to a sensor having an array of electrochemical cells for localized corrosion detection.

BACKGROUND OF THE INVENTION

Corrosion is a natural process that involves a metal atom M being oxidized, whereby it loses one or more electrons and leaves the bulk metal, $M \rightarrow M^{m+} + m\ e^-$. The lost electrons are conducted through the bulk metal to another site where they reduce (i.e. combine with) a reducible species such as a dissolved gas or a positively charged ion $G^+$ that is in contact with the bulk metal, $N + n\ e^- \rightarrow N^{n-}$ and $G^{m+} + m\ e^- \rightarrow G$.

In corrosion parlance, the site where metal atoms lose electrons is called the anode, and the site where electrons are transferred to the reducible species is called the cathode. These sites can be located close to each other on the metal's surface, or far apart depending on the circumstances. When the anodic and cathodic sites are continuous, the corrosion is more or less uniform across the surface. When these sites are far apart, the anodic sites corrode locally.

A corrosion path is essentially an electric circuit, since there is a flow of current between the cathode and anode sites. In order for a current to flow, Kirchoff's circuit laws require that a circuit be closed and that there exists a driving potential (or voltage). Part of the corrosion circuit is the base metal itself; the rest of the circuit exists in an external conductive solution (i.e. an electrolyte) that must be in contact with the metal. This electrolyte serves to take away the oxidized metal ions from the anode and provide reduction species (either nonmetalic atoms or metallic ions) to the cathode. Both the cathode and anode sites are immersed in an electrolyte for the corrosion circuit to be complete.

In corroding systems, potential gradients can be created by a number of mechanisms. These include differences in the free energy or the related electrochemical potentials for different reactions and gradients in the concentration of charged species in the solution. When two electrodes exhibiting differing potentials are electrically connected, a current flows in the external circuit.

There are various approaches to monitoring corrosion; electrochemical approaches rely on the above-described electrochemical corrosion principles and the measurement of potentials or currents to monitor corrosion damage.

One approach to monitoring corrosion is an electrical noise method, which uses electrodes to detect electrochemical noise due to localized corrosion. This method has been implemented using a single pair of near identical large electrodes, and measuring the current noise between the two electrodes. With two large electrodes, each may have a number of anodic areas and a number of cathodic areas, resulting the possibility of zero current flows between the two electrodes. In general, the overall current noise method is not well suited to indicating corrosion rate at a particular site of the metal.

U.S. Pat. No. 6,132,593 to Tan, entitled "Method and Apparatus for Measuring Localized Corrosion and Other Heterogeneous Electrochemical Processes", describes a multi-sensor electrode, comprising a number of wire beams. This multi-sensor electrode simulates a conventional one-piece electrode surface. Measurements are made by inserting a zero-resistance ammeter between a terminal of a selected wire and the coupled terminals of all other wires. Multiple measurements provide a current distribution map of electrochemical responses on the contact surface of the electrode.

When it is not practical to directly test the component of interest itself, separate sensors can be installed in the same environment. These sensors test a sample of the same material as the component of interest and can be removed from the main component structure and examined in detail. The use of such sensors facilitates the measurement of corrosion damage in a well-controlled manner over a finite sensor area.

SUMMARY OF THE INVENTION

One aspect of the invention is an electrochemical corrosion sensor that provides multiple channels of voltage output signals to a high impedance voltmeter. In one embodiment, the sensor has an insulating base. An array of metallic electrodes is arranged within the base, and the electrodes are supported within the base such that each electrode has a small area exposed on one surface of the base and such that each electrode is electrically insulated from other electrodes within the base. A common electrical lead connects each electrode to the voltmeter. A second electrical lead associated with each electrode connects the electrode to the voltmeter across a resistor associated with the electrode. The electrical connections provide a voltage measurement for each electrode across the resistor associated with that electrode.

In another embodiment, the sensor has a base that is identical in metallurgical characteristics to the equipment or part of interest. Each electrode is mounted on this base such that it is electrically insulated from the base. Additional embodiments of the invention are described herein.

An advantage of the invention is that the sensor simulates a bulk metal undergoing corrosion. It is useful for monitoring localized corrosion of metallic materials in various industries, such as the chemical, oil and gas, and power generation industries. It may be used for both field and laboratory applications.

The use of multiple resistors allows use of a voltmeter to measure the current. The measurement of currents using the multiple resistors with each of them being permanently connected to one of the electrodes eliminates the need for connection and disconnection of the current circuit between each electrode and a common joint. The measurement of the current from each electrode only involves the on/off connections of the voltmeter terminals between the resistors. Therefore, the sensor of the present invention does not perturb the corrosion process during the measurement and provides accurate measurement of the corrosion current taking place at each electrode.

DETAILED DESCRIPTION OF THE INVENTION

Figure 1:
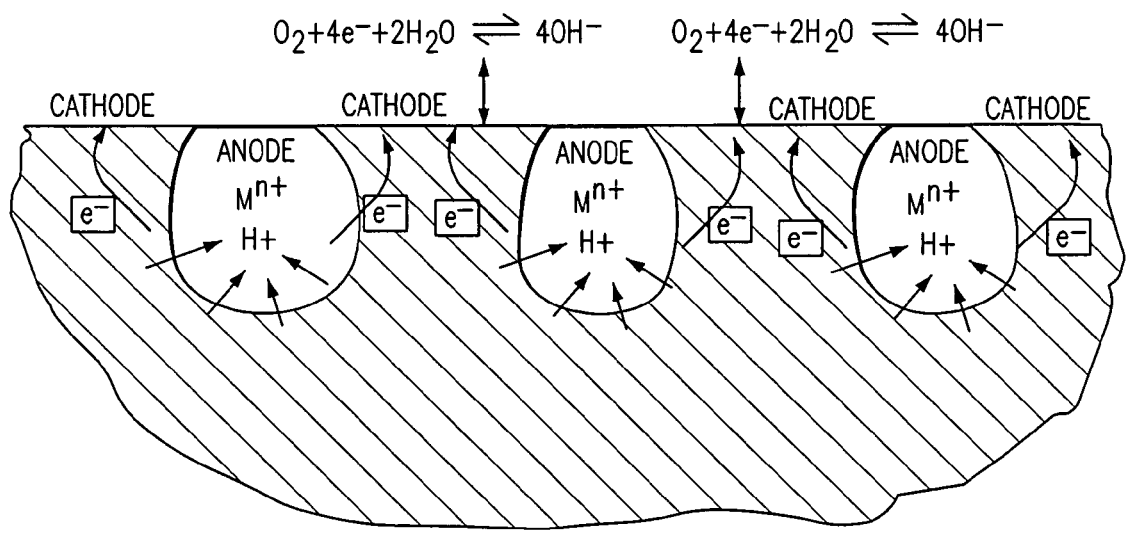
FIG. 1 illustrates pits caused by corrosion in a metallic surface.

FIG. 1 illustrates pits caused by corrosion in a metallic surface. The anodic area in each pit generates metal ions and acidity and releases electrons to the cathodic area where reduction of oxygen occurs. For simplicity, other features such as corrosion products are not shown.

More specifically, the process of localized corrosion involves the creation of actively corroding areas (anodes) separated at a distance from non-corroding areas (cathodes). At the anodic area, the metal is oxidized to metal ions with the production of electrons as illustrated below for iron and chromium.

$$Fe(s) \rightarrow Fe^{2+} + 2e^-$$

$$Cr(s) \rightarrow Cr^{3+} + 3e^-$$

The metal ions react with water, called hydrolysis reactions, to generate hydrogen ions, which increases the acidity of the solution in the localized corrosion site.

$$Cr^{3+} + 3H_2O = Cr(OH)_3 + 3H^+$$

The increase in acidity further increases local dissolution and therefore an autocatalytic process ensues. At the cathodic areas, the electrons are consumed by the cathodic half cell reactions such as, $$O_2(g) + 2H_2O + 4e^- \rightarrow 4OH^-(aq)$$

$$2H^+(aq) + 2e^- \rightarrow H_2(g)$$

$$Fe^{3+}(aq) + e^- \rightarrow Fe^{2+}(aq)$$

On a real metallic surface, there are many anodic and cathodic sites associated with corrosion. The electron flow between these sites cannot be measured directly because the sites are short circuited through the metal substrate.

Figure 2:
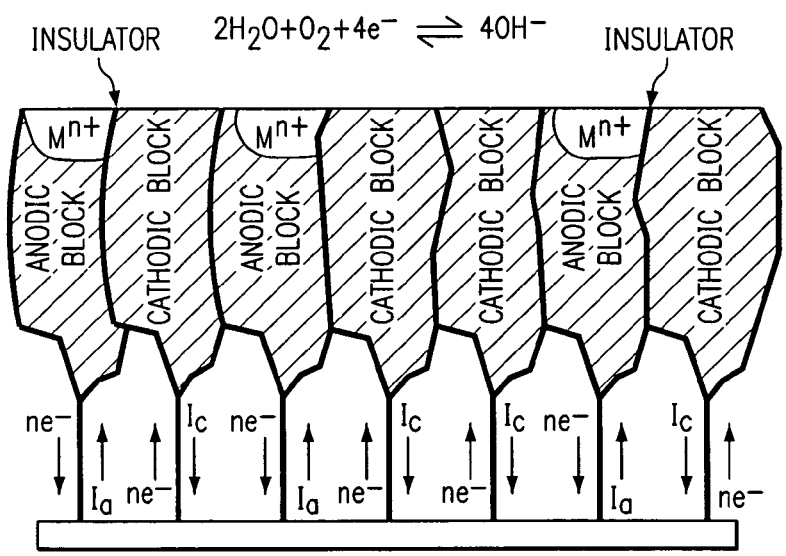
FIG. 2 illustrates how electrically insulating pieces of the surface would permit electrical measurements to be made.

FIG. 2 illustrates how electrically insulating pieces of the surface area would permit the electron flow from each anodic area or into each cathodic area to be measured. Such measurements would permit a quantitative indication of the initiation, growth, or cessation of localized corrosion in a metal surface. Theoretically, the metal could be divided into an array of small blocks separated from each other by an insulator and connected together externally. The result is an array of identical blocks that are prevented from touching each other directly but are connected externally to simulate a larger piece of metal. For each block, the integration of current flowing into a given anodic area (or from a cathodic area) over a period of time is related to the extent of growth of local corrosion at the surface of block.

Figure 3:
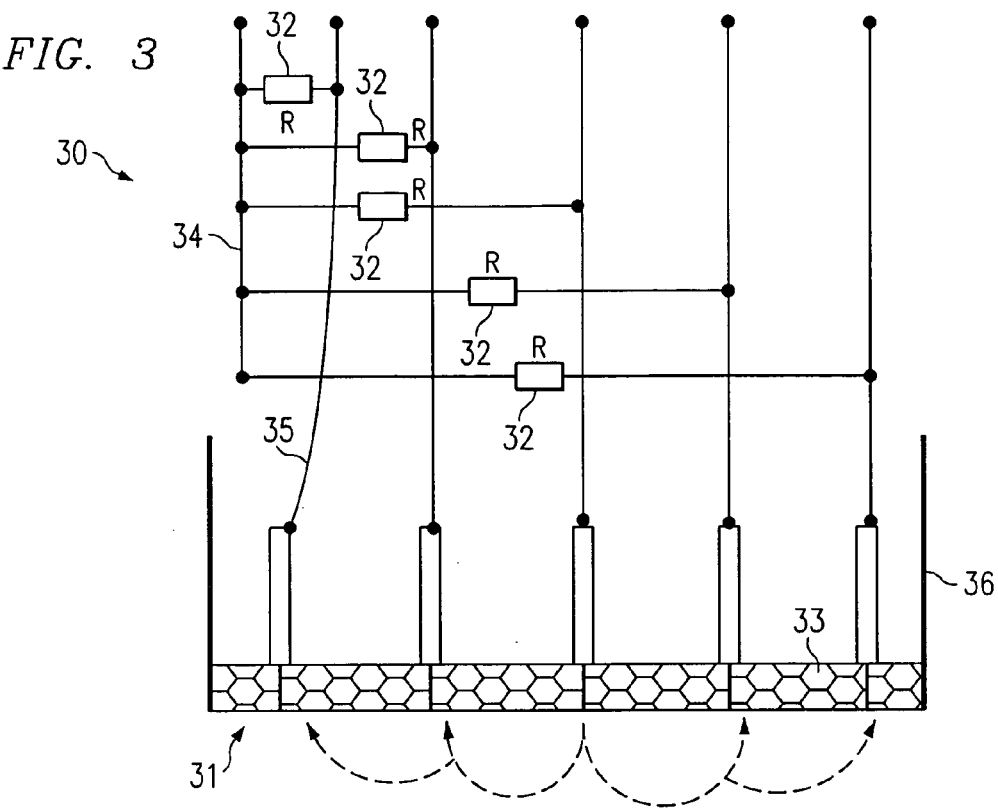
FIG. 3 illustrates a sensor in accordance with the invention.

FIG. 3 illustrates the blocks of FIG. 2, where each block is represented by an electrode 31 made from the same material as the metal of interest. Each electrode is a small piece of material or a wire, with a small surface area exposed to the electrolyte at the bottom surface of a base 33. The electrodes 31 are supported as a solid array by a solid insulating material between them, which forms an insulating base 33. An example of a suitable insulating material is an epoxy. Other insulating materials may be used as determined by environmental conditions, such as temperature and pressure.

Above the insulating base 33, each electrode 31 is connected to an electrical lead 35. As illustrated, portions of each electrode 31 encapsulated in the base 33 may be made thicker or thinner than portions outside base 33, depending on considerations such as durability, handling convenience, or fabrication.

A small resistor 32 is connected between each electrode 31 and a common electrical connection 34. The current flowing into or from each electrode can be measured by the voltage drop across the resistor 32. Each electrode output is delivered to a channel input of a voltmeter (not shown), and the voltage measurements are used to calculate current.

During experimentation using sensor 30, it was observed that crevices may form to some degree between the epoxy and metal at some of the electrodes 31. These crevices can introduce undesired additional corrosion at their sites. To minimize the formation of these crevices, sputtering or passivation methods may be used to form an inert film on the side surface of the electrode 31 before epoxy is applied.

Sensor 30 can also be implemented without a solid base 33. Various alternative means of supporting the array of electrodes 31 could be devised. For example, the electrodes 31 could be attached to each other in a grid like fashion, with supporting branches of insulating material between them.

In operation, sensor 30, whose electrodes 31 are made from the same material as a structure of interest, may be placed in the same environment as the structure of interest. Sensor 30 may then be used to monitor corrosion of electrodes 31, thereby indicating corrosion of the structure of interest. For example, to monitor corrosion within a pipeline, electrodes 31 are made from the same material as the inner surface of the pipeline and sensor 30 is inserted as a probe into the pipeline.

When a large number of electrodes 31 are used, some of the electrodes 31 may exhibit more anodic or cathodic properties than others. The differences in electrochemical response of these electrodes will differ depending on the corrosivity of the environment. For example, in a saline solution that causes localized corrosion, the presence of certain inclusions in the metal will cause very anodic behavior. However, these same inclusions will not cause such an anodic response in another more benign solution.

A feature of the sensor 30 is that rather than measuring current between pairs of electrodes, the current is measured between each electrode 31 and all other electrodes 32 of the same metal. This simulates the localized corrosion processes occurring at different sites of the metal when sensor 30 is placed in a corrosion environment.

By addressing each electrode 31 in a rectangular or circular grid successively through electrical means and tracking their locations, spatial variation in localized corrosion can be tracked. This eliminates the need for mechanical scanning devices, which are needed in the case of a single electrode.

The anodic current into each corroding electrode 31 is directly proportional to the corrosion rate at that site. This may be expressed as follows:

Corrosion Rate=Corroding Area Factor×Conversion Factor×Anodic Current Density

For pitting type corrosion, The Corroding Area Factor may be estimated from the ratio of the area of the total pits to the area of the total electrode surface.

Sensor 30 measures averaged DC current flowing into specific corrosion sites. It is thus able to detect a corrosion rate at specific sites of a metal. The coupling of a large number of electrodes 31 guarantees that there are always some electrodes 31 representing corrosion sites of a metal in a corrosion environment.

In experimentation, sensor 30 was implemented with 25 electrodes 31, in a 5×5 array. Electrodes 31 were made from stainless steel 304 wire. Sensor 30 was placed in de-ionized water, and analysis was made of the currents of the 25 electrodes 31 and the responses of the current signals to the changes in the solution chemistry. Simple parameters such as 5 percentile anodic currents or the standard deviation among the 25 electrodes were useful as effective localized corrosion indicators.

Derivation of the corrosion rate on the basis of the variance of the currents allows the use of a single parameter (standard deviation or nth percentile anoidic current) to represent localized corrosion rate. This greatly simplifies the method so that a plant or field operator having only limited knowledge of corrosion may easily understand the signal from the sensor.

Figure 4:
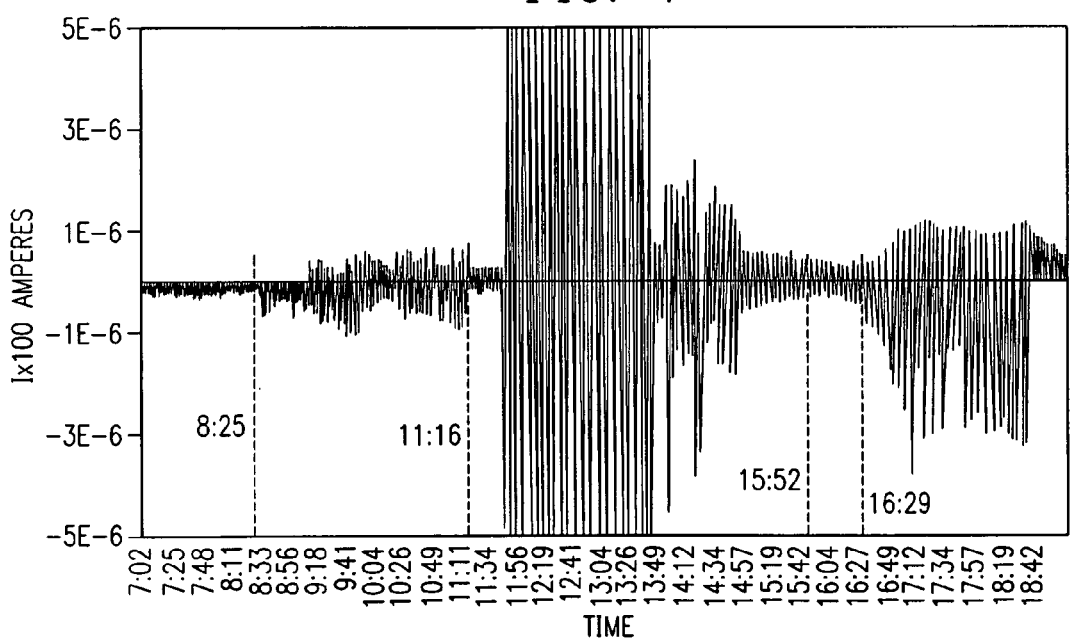
FIG. 4 illustrates how the current values from the electrode indicate the extent of corrosion.
Figure 5:
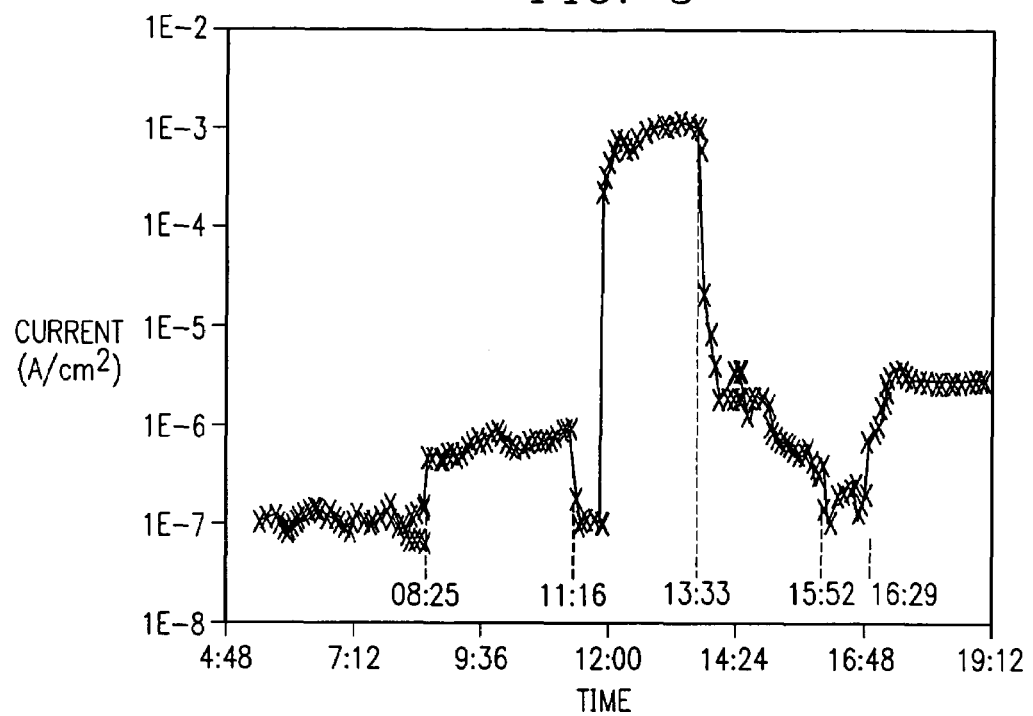
FIG. 5 illustrates how variances of the electrode outputs may be analyzed to indicate corrosion.

FIGS. 4 and 5 illustrate experimental results of placing sensor 30 in various corrosive environments. FIG. 4 plots current responses, showing only the maximum and minimum measured values among all electrodes 31 of a sensor 30 having 25 electrodes. Other electrode measurements would fall between these values. FIG. 5 plots current standard deviations. A plot similar to that of FIG. 5 could be based on current percentile, such as a five percentile plot.

As illustrated in FIGS. 4 and 5, sensor 30 was placed in the following series of corrosive environments:
de-ionized water (DI water);
potassium chloride (KCl) at t=8:25;
de-ionized water at t=11:16;
0.25 molar concentration of ferric chloride ($FeCl_3$) at t=11:40;
0.25 molar of ferric chloride (FeCl3) and sodium nitrate ($NaNO_3$) at t=13:33;
de-ionized water at t=15:52;
0.0025 molar of ferric chloride (FeCl3) at t=16:29.

The measurements depicted in FIG. 4 are among electrodes 31 and represent the varying responses, which include both anodic and cathodic responses. For the experimental sensor described above, the 25 electrodes provide 25 current measurements, each providing a different variance from the mean value. The variances among electrodes 31 are then analyzed. In general, a large variance indicates the existence of anodic and cathodic activity, and thus localized corrosion.

As illustrated, sensor 30 responded well to changes in the severity of localized corrosion according to the following trend:

De-ionized water<KCl solution<0.0025 M $FeCl_3$ solution<0.25 M $FeCl_3$ solution.

Sensor 30 also responded to the addition of a corrosion inhibitor, $NaNO_3$, as indicated by a decrease in the signals following the addition.

The above description emphasizes the use of sensor 30 as a sensor for localized corrosion of a substrate of identical material. However, sensor 30 may also be used to detect any environmental corrosivity. For example, sensor 30 could be used to evaluate the adequacy of a corrosion inhibitor in real time. Sensor 30 can be supplemented with pH and redox sensors to provide additional information on processes leading to corrosion.

The sensitivity of sensor 30 may depend on the size of electrodes 31. If each electrode 31 can be reduced to the size of the anode areas, a localized corrosion rate can be estimated by dividing the maximum anodic current by the electrode area. For very small electrodes 31, sensor 30 could be easily fabricated using integrated circuit techniques.

Figure 6:
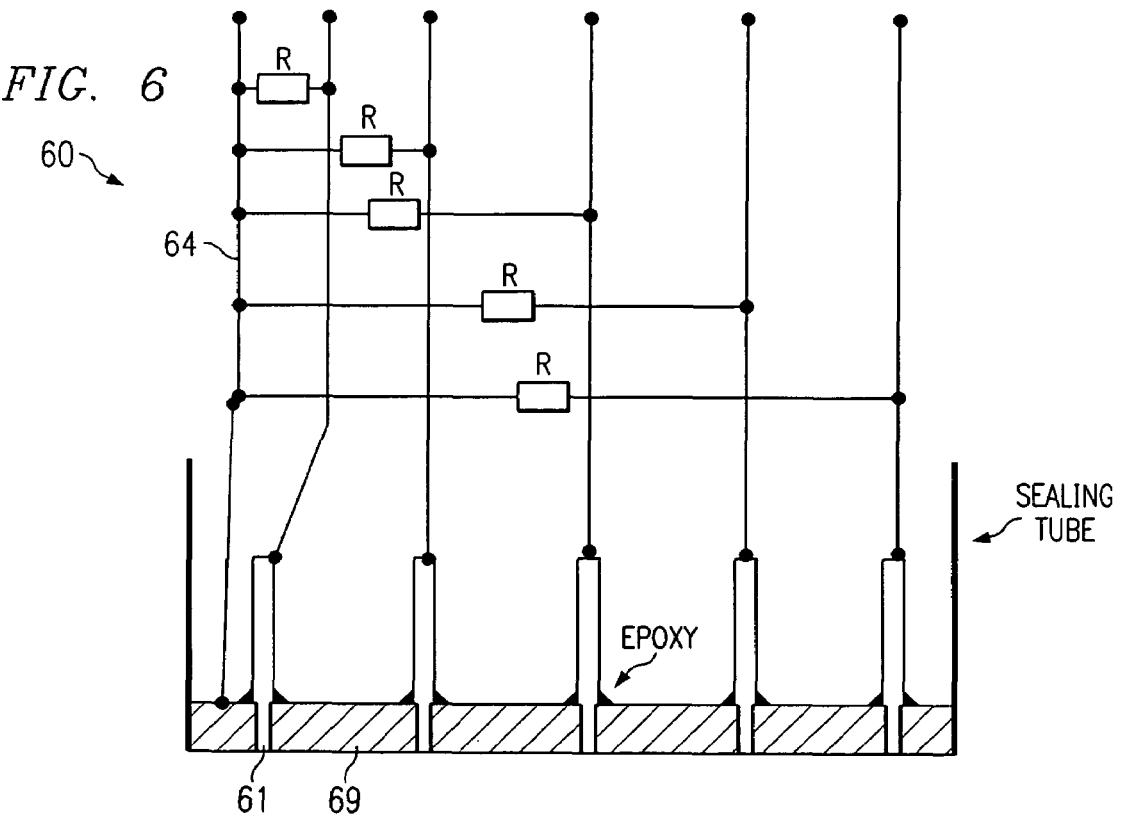
FIG. 6 illustrates an alternative embodiment of the invention.

FIG. 6 illustrates an alternative embodiment of the invention, a sensor 60. A metal block 69 is placed in the same electrolyte or humid gas as the electrodes 61 and serves as an additional electrode. It is connected to the common connection 64. It can be made of various materials. If it is made of the same material as electrodes 61, the potential of the common connection 64 will be effectively maintained at the corrosion potential of the metal of interest. If it is made from a noble metal or alloy, it will serve as a cathode and polarize electrodes 31 to a more positive value. If it is made of a more active metal, such as magnesium or zinc, it will serve as an anode and polarize electrodes 61 to a more negative value. The metal block 69 can be placed near, around, or between electrodes 61. It can also be used as the supporting base 63 with electrical insulation applied between it and each electrode 61.

Figure 8:
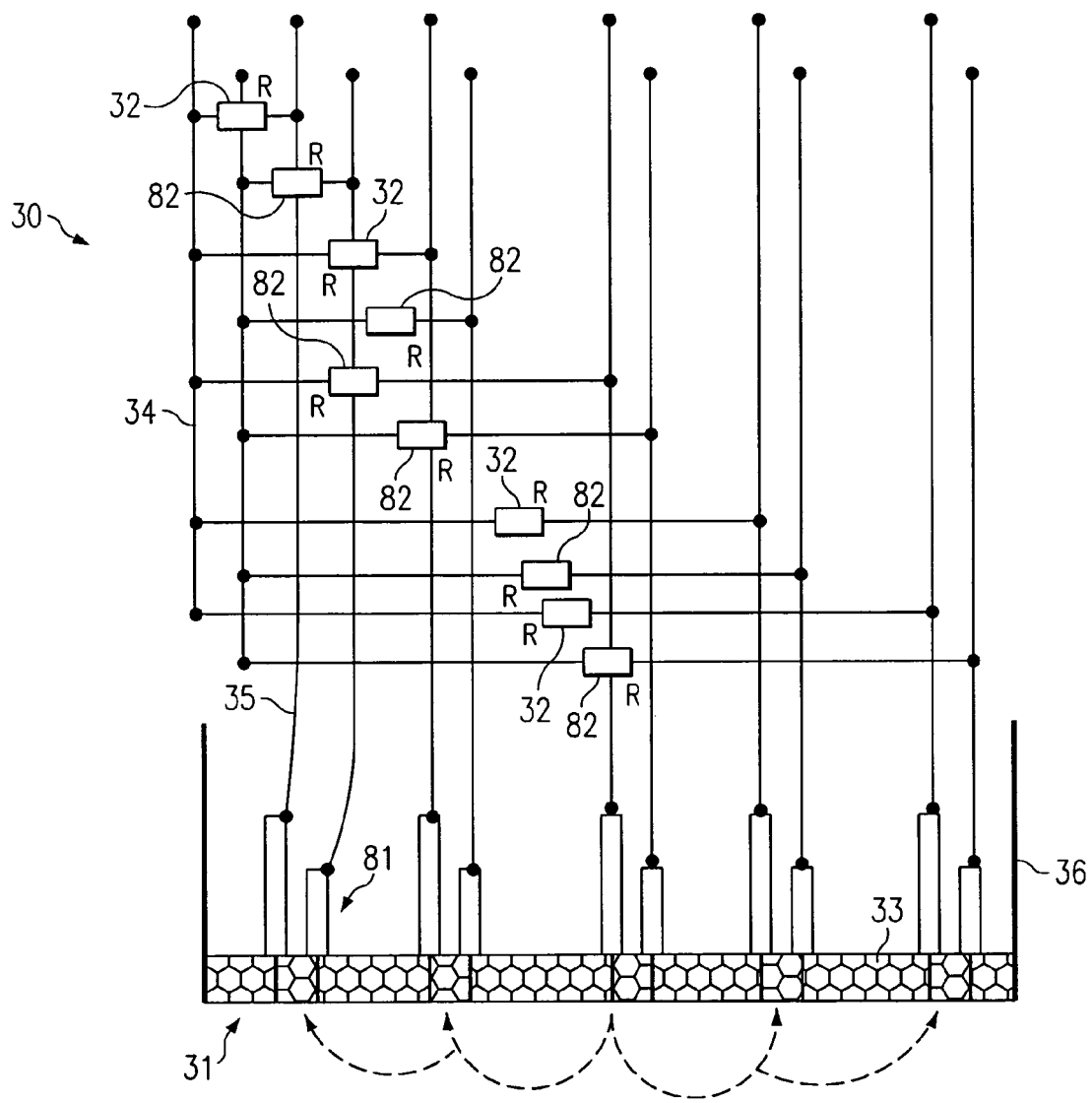
FIG. 8 illustrates an embodiment having more than one set of electrodes.

Metal block 69 may itself comprise an array of electrodes connected together. Or, referring to FIG. 8, additional electrodes 81, made from a material different from that of electrodes 31, may be embedded in base 33 between electrodes 31. These additional electrodes 81 may be made from various materials, such as noble metals. They may be connected through resistors 82 to a voltmeter in a manner similar to electrodes 31. Each subset of electrodes 31 or 81 may be connected to form a sensor and the corrosion information for different metals can be obtained by manipulating the signals from each subset. The same concepts may be extended to three or more subsets of electrodes, each having one or more electrodes made from the same metal or alloy and used to detect different corrosion.

Figure 7:
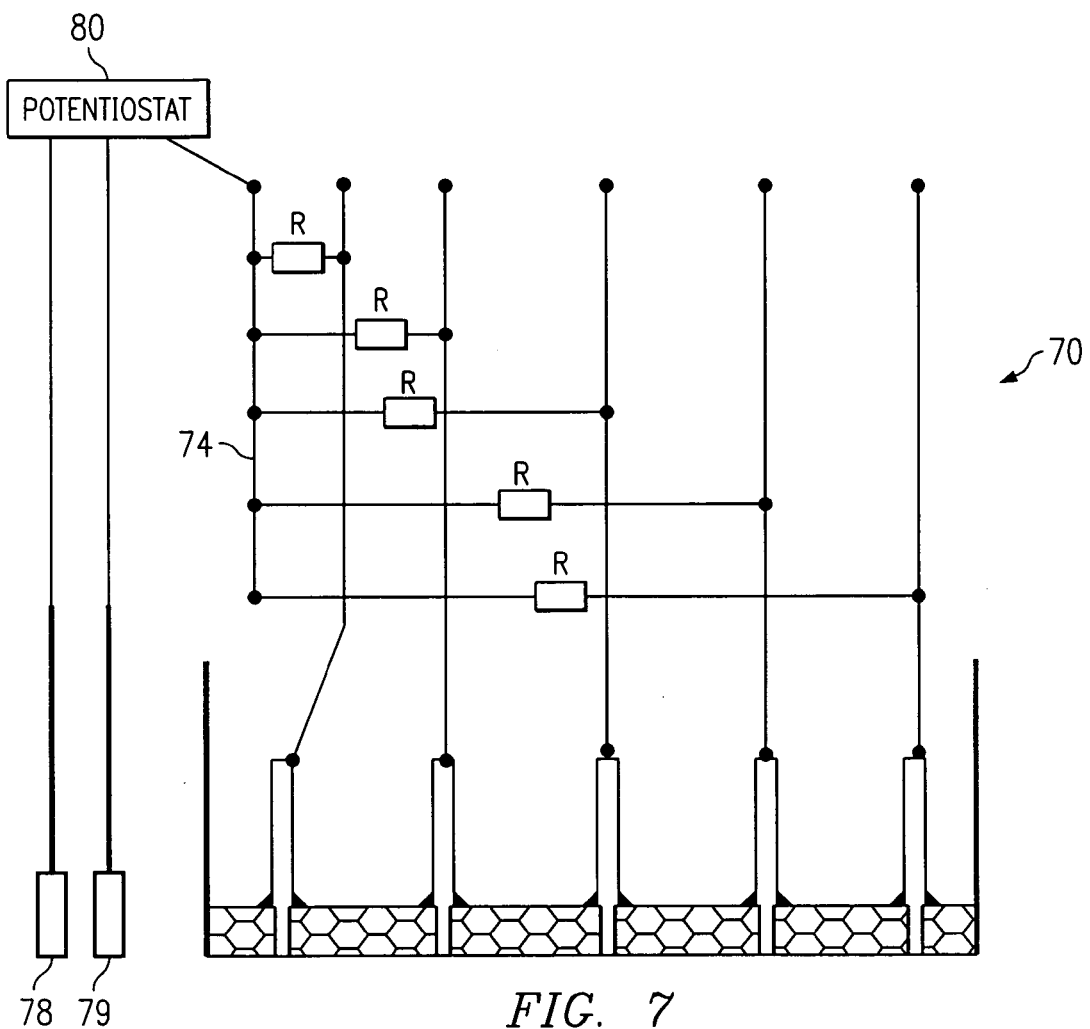
FIG. 7 illustrates an additional alternative embodiment of the invention.

FIG. 7 illustrates another alternative embodiment of the invention, a sensor 70. Sensor 70 uses a counter electrode 78 and a reference electrode 79. A potentiostat 80 or a power source is used to adjust the potential of the common electrical connection 74.

OTHER EMBODIMENTS

Although the present invention has been described in detail, it should be understood that various changes, substitutions, and alterations can be made hereto without departing from the spirit and scope of the invention as defined by the appended claims.

What is claimed is:

1. An electrochemical corrosion sensor that provides multiple channels of output voltage signals, comprising:
an array of substantially similarly structured metallic electrodes arranged such that each electrode has a surface area operable to be exposed to an electrolyte at the site of the corrosion and such that each electrode is electrically insulated from other electrodes, wherein a plurality of the electrodes are operable as anodes and a plurality of the electrodes are operable as cathodes; and
a common electrical lead connecting each electrode through a resistor to a common node, such that a voltage output signal from each electrode may be measured across a resistor associated with the electrode;
wherein the common node couples the terminals of the electrodes through the resistors to simulate a one-piece metal electrode in electrochemical behavior.

2. The sensor of claim 1, wherein the electrodes are each made from the same material.

3. The sensor of claim 1, wherein each resistor has substantially the same resistance value.

4. The sensor of claim 1, further comprising a base that supports the electrodes such that an exposed surface of each electrode is exposed at a surface of the base.

5. The sensor of claim 4, wherein the base and electrodes are fabricated as an integrated circuit.

6. The sensor of claim 4, wherein the electrodes are lengths of metal extending vertically through the base.

7. The sensor of claim 4, wherein the electrodes extend from one surface of the base and have a thickened cross sectional area above the top surface of the base.

8. The sensor of claim 4, wherein the base is made from an electrically non conductive material.

9. The sensor of claim 4, wherein the base is made from a conductive material and each electrode has an outer coating that electrically insulates the electrode from the base.

10. The sensor of claim 1, further comprising at least one additional array of electrodes interleaved within the electrodes.

11. The sensor of claim 10, wherein the second array of electrodes is made from a material different from the material from which the electrodes are made.

12. The sensor of claim 10, wherein the electrodes of the second array are made from noble metals.

13. The sensor of claim 10, wherein the electrodes of the second array are made from a pH responding material.

* * * * *